United States Patent
Kanakasabai et al.

(10) Patent No.: US 10,620,281 B2
(45) Date of Patent: Apr. 14, 2020

(54) SYSTEMS AND METHODS FOR HANDLING PEAK POWER REQUIREMENTS OF A MEDICAL IMAGING DEVICE

(71) Applicant: General Electric Company, Schenectady, NY (US)

(72) Inventors: Viswanathan Kanakasabai, Bangalore (IN); Rajendra Naik, Bangalore (IN); Juan Sabate, Niskayuna, NY (US); Michael Rose, Waukesha, WI (US); Jayanti Ganesh, Bangalore (IN)

(73) Assignee: General Electric Company, Schenectady, NY (US)

( * ) Notice: Subject to any disclaimer, the term of this patent is extended or adjusted under 35 U.S.C. 154(b) by 286 days.

(21) Appl. No.: 15/475,905

(22) Filed: Mar. 31, 2017

(65) Prior Publication Data

US 2017/0285119 A1    Oct. 5, 2017

(30) Foreign Application Priority Data

Mar. 31, 2016    (IN) .............................. 201641011515

(51) Int. Cl.
 *G01R 33/36* (2006.01)
 *H02J 7/00* (2006.01)
 *G01R 33/385* (2006.01)
 *H02J 7/34* (2006.01)
 (Continued)

(52) U.S. Cl.
 CPC ............ *G01R 33/3614* (2013.01); *A61B 6/56* (2013.01); *G01R 33/28* (2013.01);
 (Continued)

(58) Field of Classification Search
 CPC ............ G01R 33/3614; G01R 33/3852; G01R 33/5616; A61B 6/56; A61B 6/032; H02J 7/0068; H02J 7/34
 (Continued)

(56) References Cited

U.S. PATENT DOCUMENTS 5,270,657 A * 12/1993 Wirth ................. G01R 33/3852
                                                                324/318
6,037,850 A *  3/2000 Honmei ............. G01R 33/3815
                                                                324/320
(Continued)

FOREIGN PATENT DOCUMENTS

JP     2004022308 A    1/2004
WO    2015107980 A1   7/2015

OTHER PUBLICATIONS

Ristic et al., "Supercapacitor Energy Storage for Magnetic Resonance Imaging Systems", IEEE Transactions on Industrial Electronics, vol. 61, No. 8, p. 4225, Aug. 2014.
(Continued)

*Primary Examiner* — Gregory H Curran

(57) ABSTRACT

A method of handling a peak power requirement of a medical imaging device 106 is presented. The method includes determining, using at least one controlling unit 107, 108, a first voltage corresponding to a direct current (DC) link 116, a second voltage corresponding to one or more energy storage devices 110, or a combination thereof, where a power source 102 is coupled to a plurality of loads via the DC link, and the energy storage devices are coupled to the DC link. Further, the method includes comparing, using the at least one controlling unit, the first voltage with a first reference value and the second voltage with a second reference value and regulating, using at least one controlling unit, at least one of the first voltage and the second voltage based on the comparison, to handle the peak power requirement of the medical imaging device.

19 Claims, 8 Drawing Sheets

(51) Int. Cl.
*G01R 33/28* (2006.01)
*A61B 6/00* (2006.01)
*G01R 33/561* (2006.01)
*A61B 6/03* (2006.01)

(52) U.S. Cl.
CPC ........ *G01R 33/3852* (2013.01); *H02J 7/0068* (2013.01); *H02J 7/34* (2013.01); *A61B 6/032* (2013.01); *G01R 33/5616* (2013.01)

(58) Field of Classification Search
USPC .......................... 324/300–322; 600/407–435
See application file for complete search history.

(56) References Cited

U.S. PATENT DOCUMENTS

| | | | |
|---|---|---|---|
| 9,444,333 B2* | 9/2016 | Audy | H02M 3/156 |
| 2014/0009151 A1 | 1/2014 | Van Helvoort et al. | |
| 2014/0285167 A1* | 9/2014 | Audy | H02M 3/156 |
| | | | 323/282 |
| 2015/0054509 A1 | 2/2015 | Smits et al. | |

OTHER PUBLICATIONS

Senjing et al., "Optimal control strategy of dual-active-bridge converter for battery energy storage system", China International Conference on Electricity Distribution (CICED), p. 1220, Sep. 2014.

Chinese patent application 201710206205.9 Office Action dated May 5, 2019; 6 pages.

\* cited by examiner

SYSTEMS AND METHODS FOR HANDLING PEAK POWER REQUIREMENTS OF A MEDICAL IMAGING DEVICE

CROSS-REFERENCE TO RELATED APPLICATIONS

This application claims priority to India patent application number 201641011515, filed on Mar. 31, 2016, the entirety of which is incorporated herein by reference.

BACKGROUND

Embodiments of the present specification generally relate to a medical imaging system, and in particular to control techniques for achieving peak power requirements of components of the medical imaging systems such as, but not limited to, a magnetic resonance imaging (MRI) system.

Typically, MRI systems are used in medical applications to generate images of soft tissues in the human body. The MRI system includes components such as a gradient amplifier, a gradient control unit, a radio frequency (RF) transmit chain, a RF receive chain, a system control unit, and a patient handling unit. The various components of the typical MRI system may impose considerable, but transitory power requirements on the MRI system. Typically, a power distribution unit (PDU) is used to supply an alternating current (AC) to the various components of the MRI system. As will be appreciated, the system power requirements of the MRI system when no scan is being performed are minimal. However, certain scan protocols performed by the MRI system result in momentary high power requirement, resulting in high currents drawn from the AC mains. In particular, during these scan protocols, peak power may be drawn from the AC mains, where the peak power requirement of the MRI system is much higher than the average power requirement.

The increase in use of wide bore MRI systems for neurological scans may result in a significant increase in the gradient power requirements. This increase in gradient power requirements in turn may result in the peak power requirement increasing by multiple folds when compared to the currently available MRI systems.

The peak power requirement of the MRI system calls for an increased installation requirement of large capacity breakers, fuses, UPS, distribution transformers, and cabling in hospitals/clinics. Certain currently available techniques for handling the peak power requirement employ energy storage devices such as a battery, an ultra-capacitor, a capacitor bank, or similar storage devices in conjunction with the MRI systems to reduce the peak power drawn from the AC mains. However, controlling use of the energy storage device of the MRI system is a challenging task.

SUMMARY

In accordance with aspects of the present specification, a method of handling a peak power requirement of a medical imaging device is presented. The method includes determining, using at least one controlling unit, a first voltage corresponding to a direct current link, a second voltage corresponding to one or more energy storage devices, or a combination thereof, where a power source is operatively coupled to a plurality of loads via the direct current link, and where the one or more energy storage devices are operatively coupled to the direct current link. Further, the method includes comparing, using the at least one controlling unit, the first voltage with a first reference value and the second voltage with a second reference value and regulating, using the at least one controlling unit, at least one of the first voltage and the second voltage based on the comparison to handle the peak power requirement of the medical imaging device.

In accordance with another aspect of the present specification, a system for handling a peak power requirement of a medical imaging device is presented. The system includes a power source, a power distribution unit, a direct current link configured to operatively couple the power source to a plurality of loads, one or more energy storage devices operatively coupled to the direct current link and at least one controlling unit. The controlling unit is configured to determine a first voltage corresponding to the direct current link, a second voltage corresponding to the one or more energy storage devices, or a combination thereof, compare the first voltage with a first reference value and the second voltage with a second reference value, and regulate at least one of the first voltage and the second voltage based on the comparison to handle the peak power requirement of the medical imaging device.

In accordance with yet another aspect of the present specification, a controlling unit for handling a peak power requirement of a medical imaging device is presented. The controlling unit includes a measurement subunit configured to determine a first voltage corresponding to a direct current link, a second voltage corresponding to one or more energy storage devices, or a combination thereof, where a power source is operatively coupled to a plurality of loads via the direct current link, and where the one or more energy storage devices are operatively coupled to the direct current link. The controlling unit also includes a comparison subunit configured to compare the first voltage with a first reference value and the second voltage with a second reference value. Furthermore, the controlling unit includes a regulating subunit configured to regulate the first voltage, the second voltage, or a combination thereof based on the comparison to handle the peak power requirement of the medical imaging device.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Unless defined otherwise, technical and scientific terms used herein have the same meaning as is commonly understood by one of ordinary skill in the art to which this specification belongs. The terms "first", "second", and the like, as used herein do not denote any order, quantity, or importance, but rather are used to distinguish one element from another. Also, the terms "a" and "an" do not denote a limitation of quantity, but rather denote the presence of at least one of the referenced items. The term "or" is meant to be inclusive and mean one, some, or all of the listed items. The use of "including," "comprising" or "having" and variations thereof herein are meant to encompass the items listed thereafter and equivalents thereof as well as additional items. The terms "connected" and "coupled" are not restricted to physical or mechanical connections or couplings, and can include electrical connections or couplings, whether direct or indirect. Furthermore, terms "circuit" and "circuitry" and "controlling unit" may include either a single component or a plurality of components, which are either active and/or passive and are connected or otherwise coupled together to provide the described function. Also, the term operatively coupled as used herein includes wired coupling, wireless coupling, electrical coupling, magnetic coupling, radio communication, software based communication, or combinations thereof.

As will be described in detail hereinafter, various embodiments of an exemplary method and system for handling a peak power requirement of a medical imaging device are presented. Specifically, systems and methods of controlling supply of power from an energy storage device for handling the peak power requirement of the medical imaging device are presented. The medical imaging device may be a magnetic resonance imaging (MRI) system, a computed tomography (CT) system, and the like. Effectively controlling the power supplied from the energy storage device that is used in conjunction with the medical imaging device aids in reducing power demand from a power source, such as alternating current (AC) power mains. Use of the systems and methods presented hereinafter aid in reducing the installation requirements in the hospitals.

Figure 1:
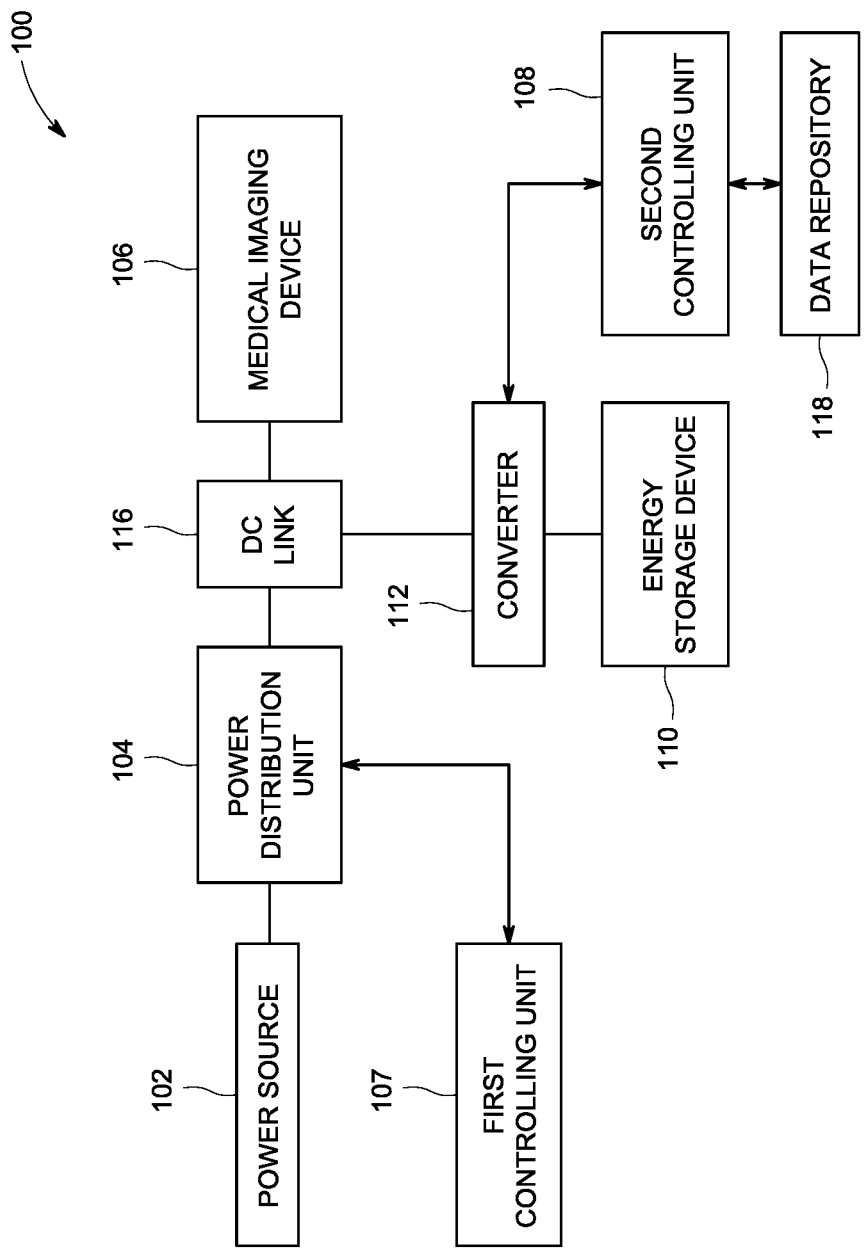
FIG. 1 is a diagrammatical representation of a system for handling a peak power requirement of a medical imaging device, according to aspects of the present specification.

Turning now to the drawings and by way of example in FIG. 1, a diagrammatical representation 100 of a system for handling a peak power requirement of a medical imaging device, according to aspects of the present specification, is presented. In one embodiment, the system 100 includes a power source 102, a power distribution unit (PDU) 104, a direct current (DC) link 116, a medical imaging device 106, and at least one controlling unit. The power source 102 is coupled to the DC link 116 via the PDU 104. Moreover, the medical imaging device 106 is coupled to the DC link 116. Furthermore, the system 100 includes an energy storage device 110. The energy storage device 110 is coupled to the medical imaging device 106 via a first converter 112 and the DC link 116. The working of the various components of the system 100, such as the power source 102, the PDU 104, the DC link 116, the energy storage device 110, and the medical imaging device 106 will be described in greater detail with respect to FIG. 3.

The power source 102 includes alternating current (AC) mains. In one embodiment, the PDU 104 is a low frequency power distribution unit (LFPDU). However, in other embodiments, the PDU 104 may be a high frequency power distribution unit (HFPDU). Use of the HFPDU also affords additional PDU functionalities such as providing galvanic isolation from the AC mains and ground fault isolation. The LFPDU typically uses a 50/60 Hz transformer, while the HFPDU uses a transformer of higher frequency operating at a few tens of kHz.

In certain embodiments, the PDU 104 includes a second converter. In one example, the second converter may include at least one of a diode rectifier and an active converter having controllable switches. Also, the second converter may be galvanically isolated from the power source 102. The energy storage device 110 includes an ultra-capacitor bank, a capacitor bank, a battery, or combinations thereof.

The medical imaging device 106 is a MRI system, a CT imaging system, and the like. Further, several components of the medical imaging device 106 may act as a plurality of loads. In the example where the medical imaging device 106 is a MRI system, components of the MRI system such as a gradient amplifier, a gradient control unit, a radio frequency (RF) transmit chain, a RF receive chain, a control subunit, patient handling unit, and a plurality of auxiliary units act as the plurality of loads.

Further, the MRI system also includes a MRI scanner. The MRI scanner in turn includes a magnet assembly, where the magnet assembly includes a plurality of coils, such as gradient coils and RF coils. The gradient coils may include an X-axis coil, a Y-axis coil, and a Z-axis coil. In one example, the gradient amplifiers may include an X-axis amplifier, a Y-axis amplifier, and a Z-axis amplifier. The X-axis amplifier, the Y-axis amplifier, and the Z-axis amplifier are in turn coupled to the X-axis coil, the Y-axis coil, and the Z-axis coil, respectively. In one non-limiting example, the amplifier corresponding to each gradient coil controls current provided to that gradient coil in accordance with signals supplied by the gradient control unit. Further, the current provided to the gradient coils may aid in creating a magnetic field with a desired gradient in the MRI scanner, and in particular, in a space where a patient is placed for scanning. This magnetic field is used in conjunction with excitation of the RF coils to generate images of a patient's body while conducting a scan operation.

During the scan operation using the MRI system, the gradient amplifier, the RF transmit chain, and the RF receive chain may draw peak power in the order of several hundreds of kilowatts (kW) for a brief period of time. In one example, during an echo planar imaging sequence in the MRI system, a power of the order of 100 kW per axis may be drawn for about 100 milliseconds (ms) from the power source 102. However, during a no scan period, the power drawn by these loads is of the order of a few hundred watts.

In accordance with aspects of the present specification, the energy storage device 110 used in the system 100 aids in handling peak power requirement of the medical imaging device 106. Particularly, the energy storage device 110 aids in providing any additional power to the medical imaging device 106, thereby reducing the peak power drawn from the power source 102. More particularly, the system 100 is configured such that only average power of the peak power requirement is supplied by the power source 102 and any remaining power requirement is provided by the energy storage device 110. In accordance with aspects of the present specification, the controlling unit 108 of the system 100 is used to regulate the supply of power from the energy storage device 110 in order to handle peak power requirement of the medical imaging device 106.

As previously noted, the system 100 may include at least one controlling unit. In a presently contemplated configuration, the system includes a first controlling unit 107 and a second controlling unit 108. Moreover, in certain embodiments, each of the first and second controlling units 107, 108 includes one or more processing units. The processing units may be configured to perform the functions of the first and second controlling units 107, 108. As used herein, the term "processing unit" refers not only to integrated circuits referred to in the art as being included in a computer, but also refers to a controller, a microcontroller, a microcomputer, a programmable logic controller (PLC), an application specific integrated circuit, application-specific processors, digital signal processors (DSPs), Application Specific Integrated Circuits (ASICs), Field Programmable Gate Arrays (FPGAs), and/or any other programmable circuits. In one example, the first controlling unit 107 is configured to control the operation of the PDU 104, while the second controlling unit 108 is configured to control the operation of the energy storage device 110.

In one embodiment, the second controlling unit 108 is configured to control supply of power from the energy storage device 110 to handle peak power requirement of the medical imaging device 106. In particular, in the event of demand for peak power from the power source 102, the second controlling unit 108 is configured to supply any excess power requirement by discharging the energy storage device 110, thereby reducing the power supplied from the power source 102.

Furthermore, the system 100 includes a data repository 118. The data repository 118 is configured to store any data required for handling the peak power requirement of the medical imaging device 106. In one example, the data repository 118 includes a memory device. Further, the memory device(s) may generally include memory element(s) including, but are not limited to, computer readable medium (e.g., random access memory (RAM)), computer readable non-volatile medium (e.g., a flash memory), one or more hard disk drives, a floppy disk, a compact disc-read only memory (CD-ROM), compact disk-read/write (CD-R/W) drives, a magnet$_0$-optical disk (MOD), a digital versatile disc (DVD), flash drives, optical drives, solid-state storage devices, and/or other suitable memory elements.

Implementing the system 100 as described with respect to FIG. 1, the efficiency of handling peak power requirement in the medical imaging device 106 is enhanced by supplying any additional power requirement from the energy storage device 110 instead of the power source 102. Thus, the power source 102 provides only an average power instead of providing the peak power demanded by the loads corresponding to the medical imaging device 106. In accordance with aspects of the present specification, two exemplary methods for controlling the supply of power from the energy storage device 110 to handle the peak power requirement of the medical imaging device 106 are presented. In certain embodiments, these methods may be performed by at least one of the first and second controlling units 107, 108 of the system 100. These two control methods will be discussed in greater detail with respect to FIGS. 5 and 6.

Figure 2:
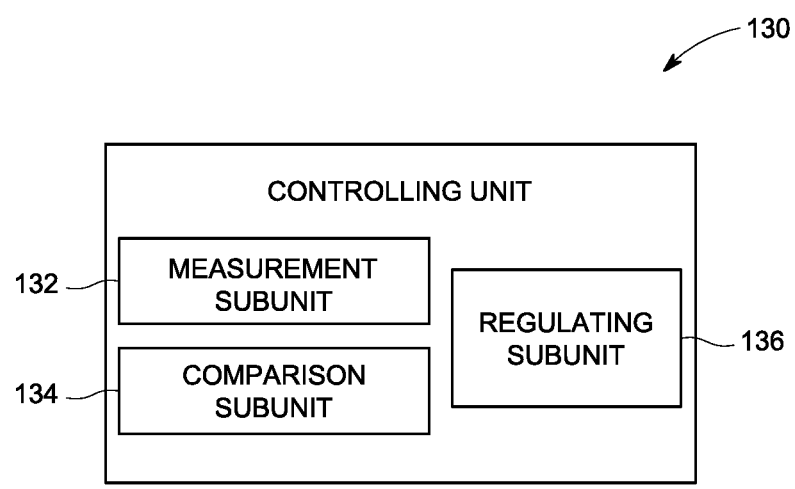
FIG. 2 is a diagrammatical representation of one embodiment of a controlling unit used in the system of FIG. 1, according to aspects of the present specification.

FIG. 2 is a diagrammatical representation 130 of one embodiment of a controlling unit for use in the system 100 of FIG. 1, according to aspects of the present specification. In particular, FIG. 2 represents an embodiment of the first and second controlling units 107, 108 used in the system of FIG. 1. As previously noted, the controlling unit 130 is configured to control the supply of power from the energy storage devices 110 to the medical imaging device 106 to mitigate the peak power requirements of the medical imaging device 106 from the power source 102. The controlling unit 130 of FIG. 2 is described with reference to the components of FIG. 1.

In a presently contemplated configuration, the controlling unit 130 includes a measurement subunit 132, a comparison subunit 134, and a regulating subunit 136. The measurement subunit 132 is configured to measure a first voltage $V_1$ corresponding to a DC link, such as the DC link 116 of FIG. 1, and/or a second voltage $V_2$ corresponding to one or more energy storage devices 110. It may be noted that in certain embodiments, the second voltage $V_2$ is a measure of a state of charge of the energy storage device 110. In certain other embodiments, other kinds of energy storage such as an inductive storage may be used. In the example where the energy storage device 110 is an inductive storage, parameters such as a current may be used to reflect the state of charge of the energy storage device.

In some embodiments, the first voltage $V_1$ and second voltage $V_2$ include a range of values having an upper limit and a lower limit. Furthermore, the comparison subunit 134 is configured to compare the first voltage $V_1$ with a first reference value $V_1^*$ and the second voltage $V_2$ with a second reference value $V_2^*$. The first reference value $V_1^*$ may be a fixed value. The second reference value $V_2^*$ includes at least one of a fixed component and a variable component. It may be noted that the variable component of the second reference value $V_2^*$ is dependent on the first voltage $V_1$ corresponding to the DC link 116. In one example, the first reference value $V_1^*$ and the second reference value $V_2^*$ are stored in the data repository 118.

Moreover, the regulating subunit 136 is configured to regulate the first voltage $V_1$ and/or the second voltage $V_2$ based on the comparison at the comparison subunit 134 to handle the peak power requirement of the medical imaging device 106. The operation of the controlling unit 130 for handling the peak power requirement of the medical imaging device via use of the energy storage device 110 will be described in greater detail with respect to FIGS. 4-6.

Figure 3:
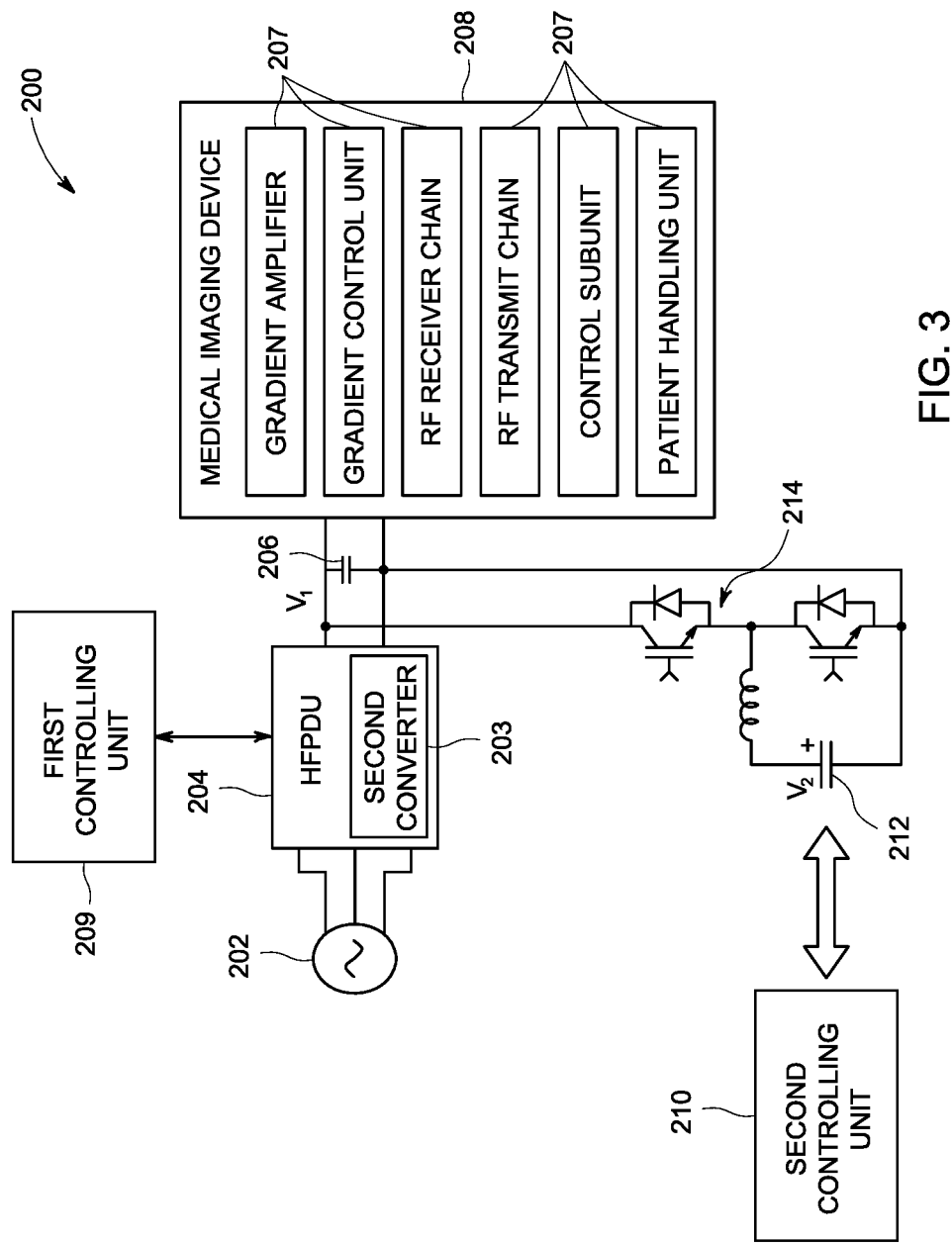
FIG. 3 is a diagrammatical representation of another embodiment of a system for handling a peak power requirement of the medical imaging device, according to aspects of the present specification.

Referring now to FIG. 3, a diagrammatical representation 200 of one embodiment of the system 100 for handling the peak power requirement of the medical imaging device 106 of FIG. 1, according to aspects of the present specification, is presented.

The system 200 includes a power source 202, a HFPDU 204, a direct current (DC) link 206, a medical imaging device 208, first and second controlling units 209, 210, and an energy storage device 212. The power source 202 is coupled to the HFPDU 204. Further, the HFPDU 204 is coupled across the DC link 206. Moreover, the medical imaging device 208 is coupled across the DC link 206. The medical imaging device 208 includes a plurality of loads 207. In the example of FIG. 3, the DC link 206 is configured to operatively couple the power source 202 to the loads 207. Furthermore, the energy storage device 212 is operatively coupled to the medical imaging device 208 via the DC link 206 and a first converter 214. The first converter 214 is a bidirectional direct current to direct current (DC-DC) converter, in one example. Moreover, the power source 202 is an AC mains.

In the example of FIG. 3, the medical imaging device 208 is a MRI device. Also, the HFPDU 204 includes a second converter 203. In one example, the second converter 203 is an active converter. In yet another example, the second converter 203 is an alternating current to direct current (AC-DC) converter. It may be noted that in an example where the system 200 includes an LFPDU, the second converter 203 may be a diode rectifier. In this example, use of the diode rectifier circumvents the need for any control by the first controlling unit 209.

The first and second controlling units 209, 210 include one or more processing units. The processing units may be configured to perform the function of the first and second controlling units 209, 210. In addition, the first and second controlling units 209, 210 are configured to control supply of power from the energy storage device 212 such that the peak power drawn from the power source 202 is maintained at average levels and any excess power is supplied by the energy storage device 212. As noted hereinabove, during a scan operation in the MRI system, peak power is drawn by the loads 207. The peak power demand by the loads 207 is provided by the power source 202 and the energy storage device 212. In one example, due to the peak power demand by the loads 207, there may be a dip in a first voltage $V_1$ across the DC link 206.

In the example of FIG. 3, the energy storage device 212 may be configured to supply any demand for excess power supply by the loads 207 in addition to the power provided by the power source 202. Accordingly, the energy storage device 212 discharges to supply the excess power demand by the loads 207 of the medical imaging device 208.

In one embodiment, the energy storage device 212 provides the power to the loads 207 via the first converter 214 and the DC link 206. Consequent to the supply of the additional power from the energy storage device 212, the voltage $V_1$ across the DC link 206 increases. Additionally, the power provided by the energy storage device 212 to the loads 207 results in a drop in the second voltage $V_2$ across the energy storage device 212. Therefore, it is desirable to recharge the energy storage device 212 to restore the second voltage $V_2$ to a rated voltage value corresponding to the energy storage device 212. In one example, the energy storage device 212 may be recharged by transferring power from the power source 202 to the energy storage device 212 via the DC link 206. In one embodiment, the energy storage device 212 may be recharged when the demand of power by the loads 207 is minimal.

Figure 4:
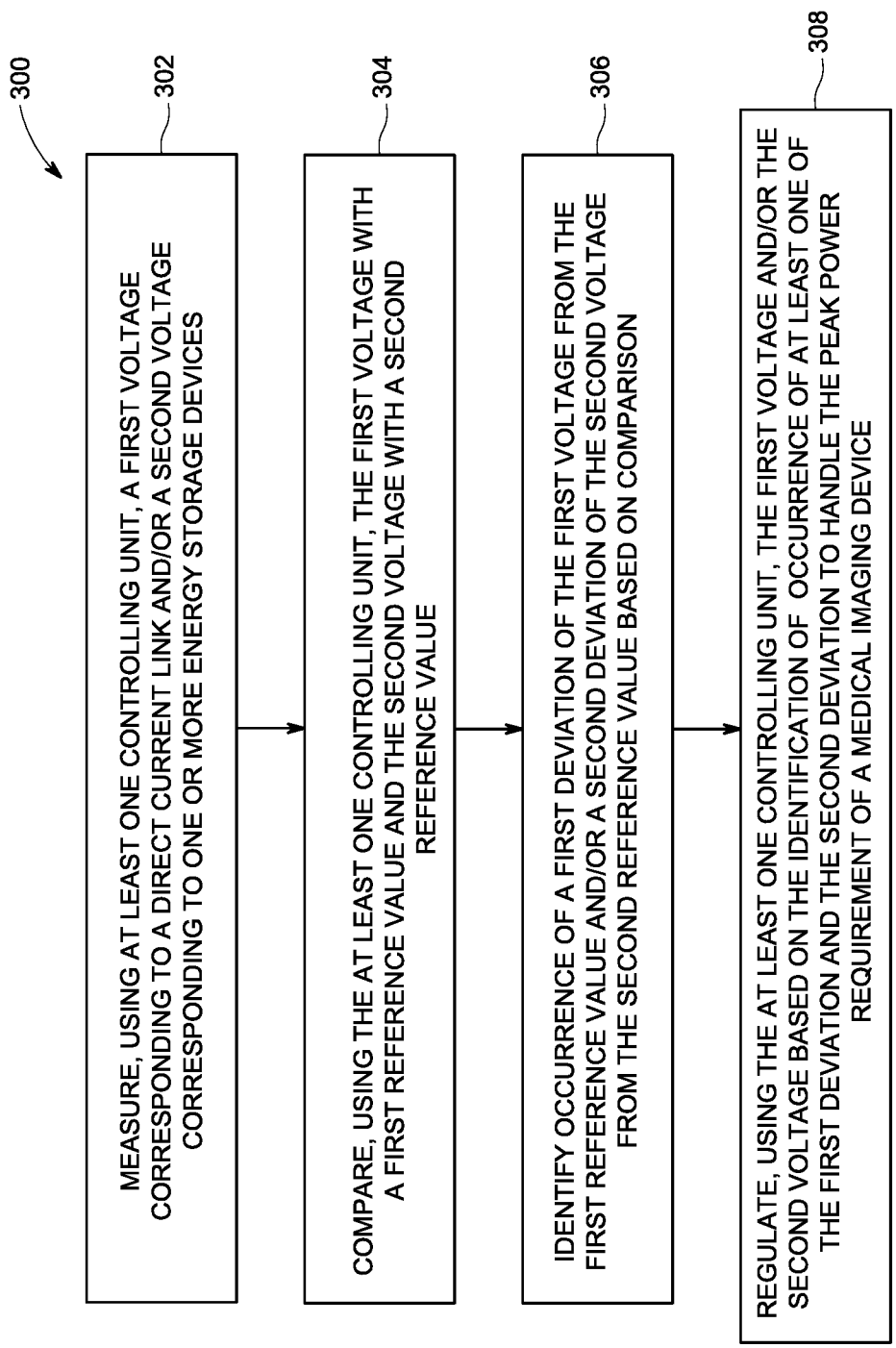
FIGS. 4-6 are flow charts representing exemplary methods for handling a peak power requirement of the medical imaging system, according to aspects of the present specification.
Figure 5:
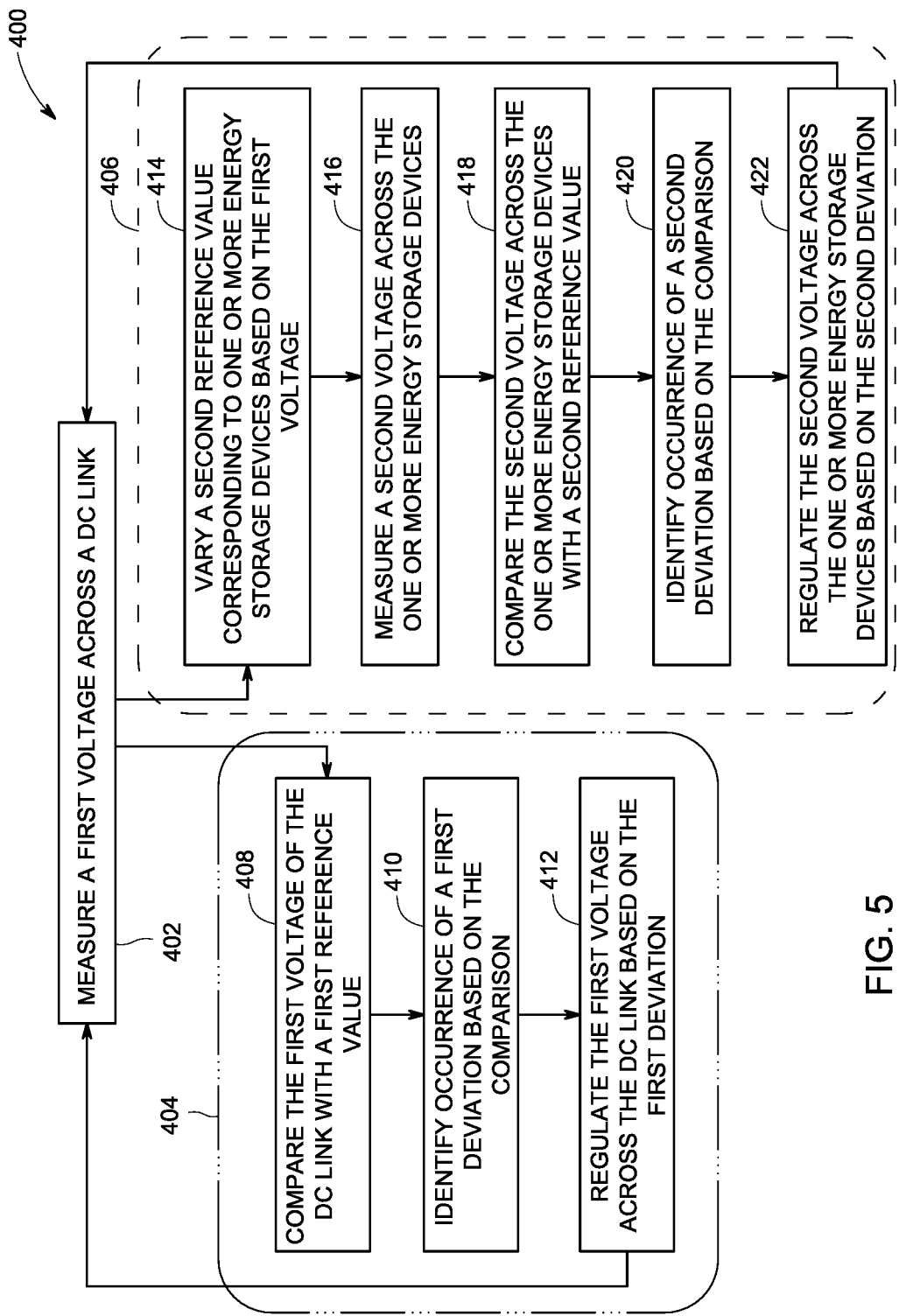
Figure 6:
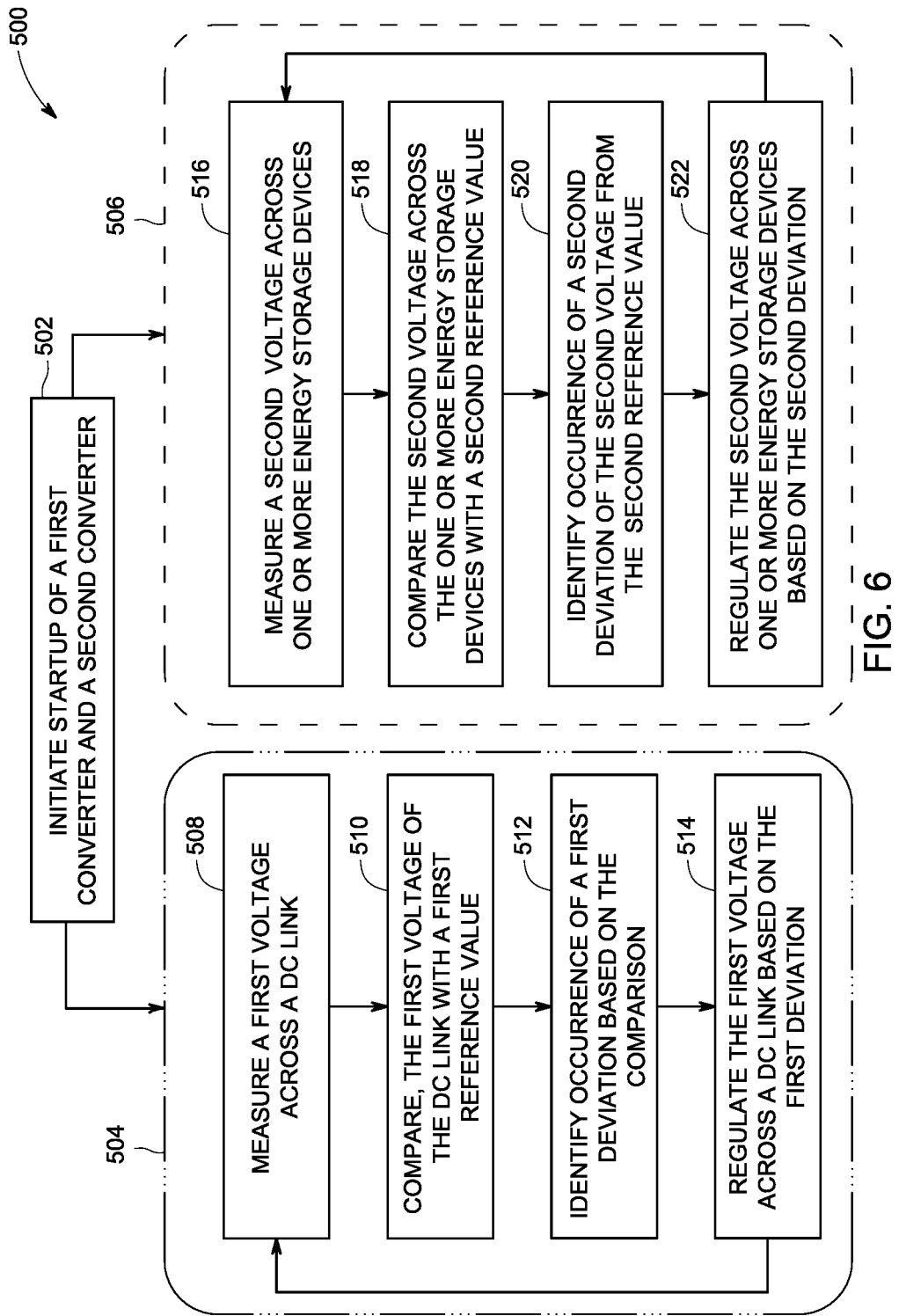

FIGS. 4-6 are flow charts representing exemplary methods for the handling a peak power requirement of a medical imaging device. Particularly, methods for handling the peak power requirements by controlling power supplied by an energy storage device are presented.

FIG. 4 depicts a flow chart 300 representing an exemplary method for handling a peak power requirement of a medical imaging device. The method of FIG. 4 will be explained with respect to the components of FIG. 3.

The method begins at block 302, where a first voltage $V_1$ corresponding to the DC link 206 and/or a second voltage $V_2$ corresponding to the energy storage device 212 are measured. In some embodiments, the first and second controlling units 209, 210 may be used to measure the first and second voltages $V_1$ and $V_2$.

Furthermore, at block 304, the first voltage $V_1$ is compared with a first reference value $V_1^*$ and the second voltage $V_2$ is compared with a second reference value $V_2^*$ using at least one of the first and second controlling units 209, 210. In addition, at block 306, occurrence of a first deviation of the first voltage $V_1$ from the first reference value $V_1^*$ and/or a second deviation of the second voltage $V_2$ from the second reference value $V_2^*$ may be identified based on comparison.

By way of example, peak power drawn by the loads 207 results in a drop in the first voltage $V_1$. This drop in the first voltage $V_1$ results in a corresponding first deviation of the first voltage $V_1$ from the first reference value $V_1^*$. In another example, any drop in the second voltage $V_2$ results in a corresponding second deviation of the second voltage $V_2$ from the second reference value $V_2^*$.

Moreover, at block 308, based on the identification of at least one of the first deviation and the second deviation, the first voltage $V_1$, the second voltage $V_2$, or a combination thereof are regulated to handle the peak power requirement of the medical imaging device 208. In certain embodiments, the first and/or second controlling units 209, 210 may be employed to regulate the first and/or second voltages $V_1$, $V_2$.

In accordance with aspects of the present specification, regulating the first voltage $V_1$ and/or the second voltage $V_2$ may entail transferring power between one or more of the power source 202, the DC link 206, the HFPDU 204, the energy storage device 212, and the first converter 214. In particular, if the first deviation is identified due to the drop in first voltage $V_1$, then the power is transferred from the energy storage device 212 to the DC link 206 and/or from the power source 202 to the DC link 206. This transfer of power aids in restoring the first voltage $V_1$ to a predefined value of first voltage $V_1$, such as the first reference value $V_1^*$. Consequent to the power transfer, the first deviation is reduced, and hence the first voltage $V_1$ is regulated.

Additionally, if a second deviation is identified due to a drop in second voltage $V_2$, then the power is transferred from the DC link 206 to the energy storage device 212. This transfer of power aids in restoring the second voltage $V_2$ to a predefined value of the second voltage $V_2$, such as the second reference value $V_2^*$. Hence, the second deviation is reduced. This reduction of the second deviation in turn results in the second voltage $V_2$ being regulated.

In one example, the first and second controlling units 209, 210 are configured to regulate at least one of the first and the second voltages $V_1$, $V_2$. Although the method of FIG. 4 is explained with respect to the medical imaging device 208 employing a HFPDU, the method of FIG. 4 is also applicable to a medical imaging device employing an LFPDU. The various blocks of FIG. 4 will be described in greater detail with respect to the FIGS. 5 and 6.

FIG. 5 is a flow chart 400 representing one example of a method for handling a peak power requirement of a medical imaging device by controlling power supplied by an energy storage device. The method 400 of FIG. 5 is described with respect to the components of FIG. 3. With reference to FIG. 3, the first controlling unit 209 is configured to control the first voltage $V_1$ across the DC link 206 and the second controlling unit 210 is configured to control the second voltage $V_2$ corresponding to the energy storage device 212.

The method begins at block 402, where the first voltage $V_1$ across a DC link 206 is measured. In some embodiments, the first voltage $V_1$ includes a range of values having an upper limit and a lower limit. In one example, the upper limit of first voltage is 670 volts and the lower limit of first voltage is 650 volts.

Subsequent to block 402, control may be transferred to a first path 404 and a second path 406. In accordance with some aspects of the present specification, steps corresponding to the second path 406 may be executed concurrently with the steps corresponding to the first path 404. However, in certain other embodiments, the steps of paths 404 and 406 may be executed in a sequential manner. Moreover, in one example, the steps corresponding to the first path 404 may be executed by the first controlling unit 209 and the steps corresponding to the second path 406 may be executed by the second controlling unit 210.

Along the first path 404, at block 408, the first voltage $V_1$ is compared with a first reference value $V_1^*$. The first reference value $V_1^*$ is a fixed value, in one example. Further, the first reference value $V_1^*$ may be retrieved from a data repository.

Moreover, at block 410, occurrence of a first deviation is identified, based on the comparison at block 408. In one example, a peak power demand by the loads 207 results in a drop in the first voltage $V_1$. In this situation, the first voltage $V_1$ may deviate from the first reference value $V_1^*$ and hence result in occurrence of the first deviation.

Subsequently, at block 412, the first voltage across the DC link 206 is regulated based on the identified first deviation. In one example, the regulation of the first voltage includes transfer of power between the power source 202 and the DC link 206. In particular, the power is transferred from the power source 202 to the DC link via the second converter 203. During this transfer of power, if the demand of power from the power source 202 is below the average power, the value of first voltage $V_1$ may be restored by the transfer of power from the power source 202 via the second converter 203. The value of the first voltage $V_1$ is restored to a predefined value of the first voltage $V_1$, such as the first reference value $V_1^*$. The restoration of the first voltage $V_1$ may aid in reducing the first deviation. Subsequent to execution of block 412, control may be reverted to block 402 and the blocks 402, 408, 410, and 412 may be repeated. It may be noted that in one embodiment, blocks 402, 408, 410, and 412 may be repeated until a shutdown of at least one of the first and second converters 214, 203 is initiated.

As previously noted, in certain embodiments, the blocks corresponding to the second path 406 may be executed concurrently with the blocks of the first path 404. At block 414, the second reference value $V_2^*$ corresponding to energy storage device 212 may be varied based on the first voltage $V_1$. Moreover, as previously noted, the second reference value $V_2^*$ includes a variable component, where the variable component is dependent on the first voltage $V_1$ corresponding to the DC link 206. One example of a relationship between the second reference value $V_2^*$ and the first voltage $V_1$ is described in greater detail with respect to FIG. 7.

Figure 7:
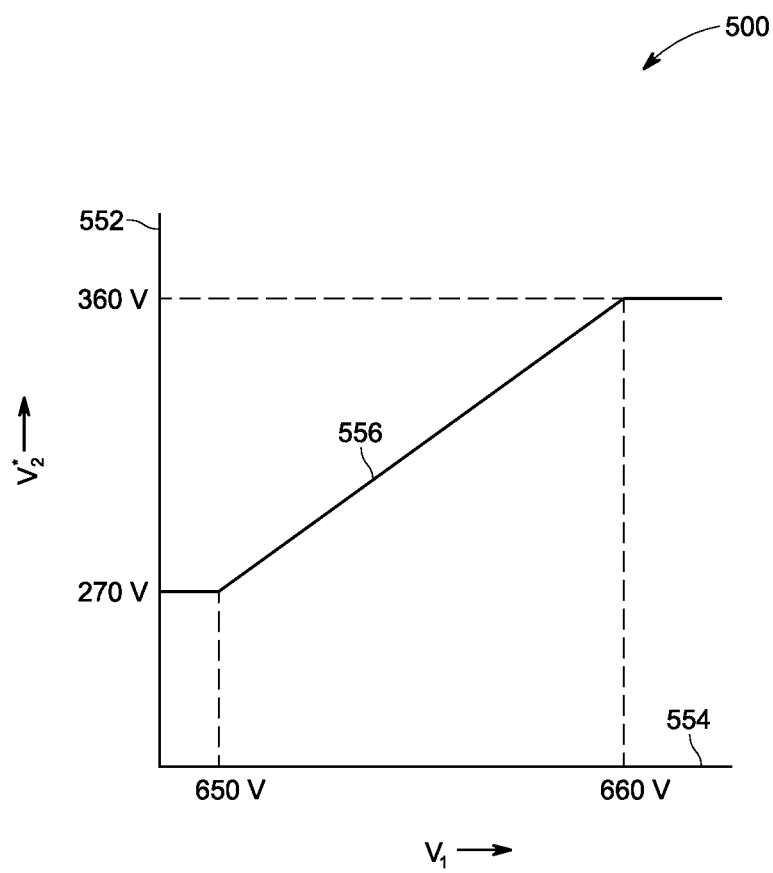
FIG. 7 is a graphical representation of one example of a relationship between a second reference value and a first voltage, according to aspects of the present specification.

Turning now to FIG. 7, a graphical representation 550 of one example of a relationship between a second reference value and a first voltage, in accordance with aspects of the present specification, is presented. In the example of FIG. 7, reference numeral 552 depicts a y-axis representing the second reference value $V_2^*$ in volts and reference numeral 554 depicts an x-axis representing the first voltage $V_1$ in volts. Furthermore, reference numeral 556 represents a determined relationship between the second reference value $V_2^*$ and the first voltage $V_1$. The example of FIG. 7, depicts a linear relationship between the second reference value $V_2^*$ and the first voltage $V_1$. In another example, the relationship between the second reference value $V_2^*$ and the first voltage $V_1$ may be an exponential relationship. In light of the determined relationship between the second reference value $V_2^*$ and the first voltage $V_1$, any change in the first voltage $V_1$ results in a corresponding change in the second reference value $V_2^*$. By way of example, when there is a linear relationship between the second reference value $V_2^*$ and the first voltage $V_1$, any drop in the first voltage $V_1$ results in a corresponding drop in the value of the second reference value $V_2^*$.

Referring back to FIG. 5, at block 416, a second voltage $V_2$ corresponding to the energy storage device 212 is measured. The second voltage $V_2$ includes a range of values having an upper limit and a lower limit. The lower limit of the second voltage $V_2$ is 270 volts, in one non-limiting example.

At block 418, the second voltage $V_2$ across the energy storage device 212 is compared with a second reference value $V_2^*$. In certain embodiments, the second reference value $V_2^*$ may be retrieved from a data repository. Moreover, at block 420, occurrence of a second deviation may be identified based on the comparison at block 418.

Furthermore, at block 422, the second voltage $V_2$ across the energy storage device 212 is regulated based on the identified second deviation. The regulation of the second voltage $V_2$ across the energy storage device 212 may include transfer of power between the energy storage device 212 and the DC link 206 based on the second deviation. If the second voltage $V_2$ across the energy storage device 212 is greater than the second reference value $V_2^*$, the power is transferred from the energy storage device 212 to the DC link 206. However, if the second voltage $V_2$ across the energy storage device 212 is lower than the second reference value $V_2^*$, the power is transferred from the DC link 206 to the energy storage device 212. This transfer of power aids in restoring the value of second voltage $V_2$ to a predefined value of second voltage $V_2$, such as the second reference value $V_2^*$. Thus, the second deviation may be reduced. Further, subsequent to the execution of block 422, control is reverted to block 402 and steps of blocks 402, 414, 416, 418, 420, and 422 may be repeated. In certain embodiments, blocks 402, 414, 416, 418, 420, and 422 are repeated until a shutdown of at least one of the first and second converters 214, 203 is initiated.

As noted hereinabove, the method for handling the peak power requirement of the medical imaging device aids in providing any additional power from the energy storage device 212, while only the average power is provided by the power source 202. In the example of the method 400 of FIG. 5, to facilitate the supply of the additional power from the energy storage device 212, the first converter 214 is configured to provide a faster rate of power conversion than the second converter 203. The faster power conversion by the first converter 214 aids in providing a faster regulation of second voltage $V_2$ than the regulation of the first voltage $V_1$. In one example, the faster regulation of the second voltage $V_2$ may in turn result in a faster rate of discharge of the energy storage device 212 to the DC link 206 when compared to the rate at which power is provided to the DC link 206 from the power source 202.

It may be noted that as described hereinabove, a peak power demand by the load 207 results in a drop in the first voltage $V_1$. This drop in the first voltage $V_1$ causes the second reference value $V_2^*$ to drop. Consequent to the drop in the second reference value $V_2^*$, the energy storage device 212 discharges energy, thereby resulting in a drop in the second voltage $V_2$. It may be noted that the discharge of energy from the energy storage device 212 in turn results in a reduction in the rate of drop of the first voltage $V_1$. Accordingly, the discharge of energy from the energy storage device 212 facilitates supply of the peak power demand by the load 207 by the energy storage device 212.

Furthermore, when the power demand from the power source 202 is below the average power, the first voltage $V_1$ is restored to a predefined value of the first voltage $V_1$, such as the first reference value. Since, the first voltage $V_1$ is restored, the second reference value $V_2^*$ recovers, and the energy storage device 212 recharges to restore the value of second voltage $V_2$. In particular, the energy storage device 212 is recharged by the transfer of power between the energy storage device 212 and the DC link 206.

Although the method of FIG. 5 is described with respect to the medical imaging device 208 employing a HFPDU, the method of FIG. 5 is also applicable to a medical imaging device employing an LFPDU. It may be noted that for the currently existing MRI system power architectures employing an LFPDU, the method of FIG. 5 aids in retrofitting a "drop in" energy storage device. Furthermore, implementing the method of FIG. 5 obviates the need for any communication between the first controlling unit 209 and the second controlling unit 210.

Turning now to FIG. 6, a flow chart 500 representing another method for handling a peak power requirement of a medical imaging device by controlling power supplied by an energy storage device is presented. Also, the method of FIG. 6 will be explained with respect to the components of FIG. 3. It may be noted that in certain embodiments, the method 500 entails a communication between a first converter 214 and a second converter 203 corresponding to the HFPDU 204. In one embodiment, when there is need for communication between the first converter 214 and the second converter 203, the first and second converters 214, 203 may be packaged as a single unit. Furthermore, in this embodiment, software and hardware corresponding to the first and second controlling units 209, 210 may exist as a single unit.

The method 500 of FIG. 6 begins at block 502 where a startup of the first converter 214 and the second converter 203 may be initiated. The term 'startup of the converter' refers to energization or activation of the converter. Once the startup is initiated, control may be transferred to a first path 504 and a second path 506. In accordance with some aspects of the present specification, steps corresponding to the second path 506 may be executed concurrently with steps of the first path 504. However, in certain other embodiments, the steps of paths 504 and 506 may be executed in a sequential manner. Moreover, in one example, the steps corresponding to the first path 504 may be executed by the second controlling unit 210 and the steps corresponding to the second path 506 may be executed by the first controlling unit 209. In particular, in the method 500 of FIG. 6, a first controlling unit 209 is configured to control a second voltage $V_2$ across an energy storage device 212. Also, a second controlling unit 210 is configured to control a first voltage $V_1$ of the DC link 206.

Along the first path 504, at block 508, a first voltage $V_1$ corresponding to the DC link 206 is measured. Furthermore, at block 510, the first voltage $V_1$ of the DC link 206 is compared with a first reference value $V_1^*$. The first reference value $V_1^*$ is a fixed value, in one example. Further, the first reference value $V_1^*$ may be retrieved from a data repository.

At block 512, an occurrence of a first deviation is identified based on the comparison. Also, at block 514, the first voltage $V_1$ across the DC link 206 is regulated based on the first deviation. The regulation of the first voltage $V_1$ includes transfer of power between the energy storage device 212 and the DC link 206. In one example, the power is transferred from the energy storage device 212 to the DC link 206 via the first converter 214.

This transfer of power to the DC link 206 aids in restoring the first voltage $V_1$ to a predefined value of the first voltage $V_1$, such as the first reference value. Consequently, the first deviation of the first voltage $V_1$ is reduced. Subsequent to execution of block 508, control is reverted to block 508 and the blocks 508, 510, 512, and 514 are repeated. In certain embodiments, blocks 508, 510, 512, and 514 are repeated until a shutdown of at least one of the first and second converters 214, 203 is initiated.

As noted hereinabove, steps corresponding to the second path 506 may be executed concurrently with the steps of the first path 504. At block 516, the second voltage $V_2$ across the energy storage device 212 is measured. The second voltage $V_2$ includes a range of values having an upper limit and a lower limit.

Furthermore, at block 518, the second voltage $V_2$ across the energy storage device 212 is compared with a second reference value $V_2^*$. In the example of FIG. 6, the second reference value $V_2^*$ includes a fixed component. The second reference value $V_2^*$ may be retrieved from a data repository.

At block 520, an occurrence of a second deviation of the second voltage $V_2$ across the energy storage device 212 from the second reference value $V_2^*$ is identified. By way of example, a drop in the second voltage $V_2$ may result in the second deviation of the second voltage $V_2$ from the second reference value $V_2^*$. In the example of the method 500, the second deviation is communicated to the first controlling unit 209.

At block 522, the second voltage $V_2$ across the energy storage device 212 is regulated based on the second deviation. The regulation of the second voltage $V_2$ includes transfer of power from the power source 202 to the energy storage device 212 via the DC link 206.

As noted hereinabove, the second controlling unit 210 corresponding to the first converter 214 is configured to control the first voltage $V_1$ across the DC link 206. In certain situations, the transfer of power from the power source 202 to the DC link 206 may result in an excess power across the DC link 206, thereby resulting in an increase in the voltage across the DC link 206. Accordingly, in this scenario, the controlling unit 210 may regulate the first voltage $V_1$ by providing the power from the DC link 206 to the energy storage device 212, thereby recharging the second energy storage device 212. Consequently, the second voltage $V_2$ is restored to a predefined value of the second voltage $V_2$, such as the second reference value $V_2^*$. This regulation of the second voltage at block 522 in turn results in a reduction in the second deviation. Furthermore, subsequent to block 522, control reverts to block 516 and the blocks 516, 518, 520, and 522 are repeated. In one embodiment, blocks 516, 518, 520, and 522 are repeated until a shutdown of at least one of the first and second converters 214, 203 is initiated.

Figure 8A:
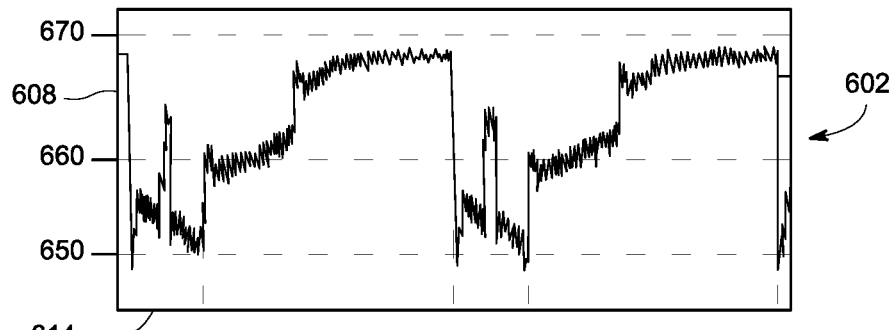
FIGS. 8(a)-8(c) are diagrammatical representations of different electrical parameters corresponding to the system of FIG. 1, according to aspects of the present specification.
Figure 8B:
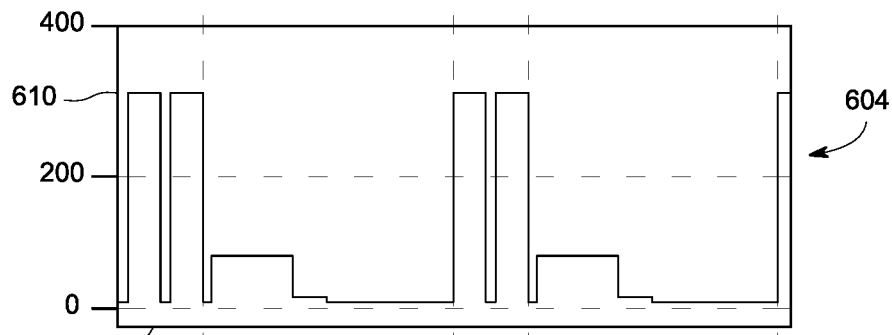
Figure 8C:
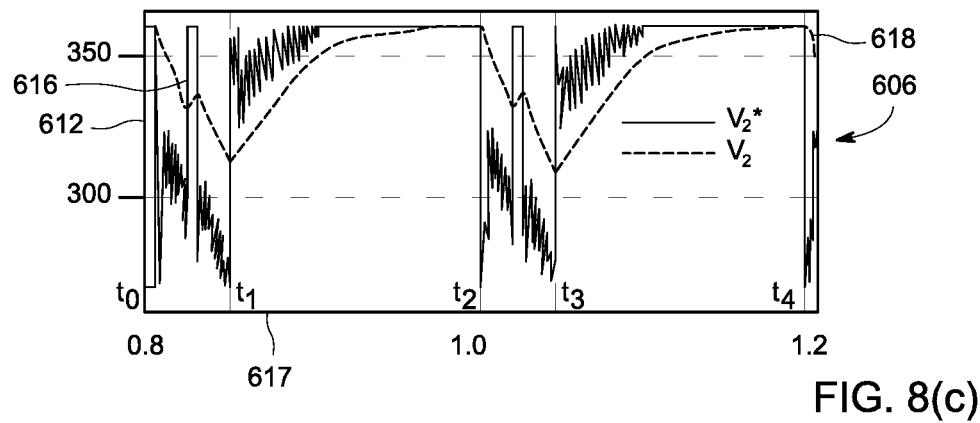

FIGS. 8(a)-8(c) are diagrammatical representations of different electrical parameters corresponding to the system 100 of FIG. 1. In particular, FIGS. 8(a)-8(c) depict simulation results of the system 100 for handling the peak power requirement of the medical imaging device 106 using the method 400 of FIG. 5. In this example, the system 100 includes a HFPDU. FIGS. 8(a)-8(c) are described with reference to the components of FIGS. 1-7.

Referring now to FIG. 8(a), reference numeral 602 is representative of a graphical representation of a first voltage $V_1$ across the DC link 206. Also, in FIG. 8(b), reference numeral 604 represents a graphical representation of a current drawn by the load 207. In a similar manner, in FIG. 8(c), reference numeral 606 is representative of a graphical representation of a voltage corresponding to the energy storage device 212. In particular, FIG. 8(c) depicts graphical representations of a second reference value $V_2^*$ 616 and a second voltage $V_2$ 618 across the energy storage device 212. In this example, the second reference value $V_2^*$ 616 is a variable component that is dependent on the first voltage $V_1$. Also, as noted hereinabove with respect to FIG. 7, the second reference value $V_2^*$ has a linear relationship with the first voltage $V_1$ such that any change in the first voltage $V_1$ results in a corresponding change to the second reference value $V_2^*$.

Reference numerals 614, 615, 617 represent an x-axis corresponding the graphical representations 602, 604, and 606, respectively. Also, reference numerals 608, 610, and 612 represent a y-axis of the graphical representations 602, 604, and 606, respectively. Reference numeral 608 represents the first voltage $V_1$ in volts, reference numeral 610 represents a current drawn by the loads 207 in amperes, and the reference numeral 612 represents the second voltage $V_2$ and second reference value $V_2^*$ in volts.

As depicted in FIG. 8(*b*), during a period $t_0$-$t_1$, the current drawn by the loads 207 from the power source 202 is increasing in a stepped fashion. Accordingly, during the period $t_0$-$t_1$, power drawn by the loads 207 may also increase in a stepped fashion. As will be appreciated, power is proportional to current. Moreover, the increase in the power drawn by the loads 207 during the period $t_0$-$t_1$, results in a dip in the value of the first voltage $V_1$ 608 during the period $t_0$-$t_1$. Also, the second reference value $V_2^*$ 616 follows the dip in the first voltage $V_1$ 608. The dip in the second reference value $V_2^*$ causes a discharge of the energy storage device 212. In particular, the energy storage device 212 discharges to follow the second reference value $V_2^*$ 616 with a dynamic delay dependent upon a size of the energy storage device 212. Consequently, the second voltage $V_2$ corresponding to the energy storage device 212 dips during the period $t_0$-$t_1$.

Furthermore, during a period $t_1$-$t_2$, the current drawn by the loads 207 is negligible. Hence, the power drawn by the loads 207 is also negligible. Therefore, during this period $t_1$-$t_2$, the first voltage $V_1$ 608 increases and is regulated to a predefined value of the first voltage $V_1$ 608. Further, during the period $t_1$-$t_2$, the second reference value $V_2^*$ 616 follows the first voltage $V_1$ 608. Therefore, during the period $t_1$-$t_2$ the second reference value $V_2^*$ 616 increases and is maintained at a determined value. The energy storage device 212 is recharged by following the second reference value $V_2^*$ with a dynamic delay. Thus, the second voltage $V_2$ 618 corresponding to the energy storage device 212 increases during the period $t_1$-$t_2$.

It may be noted that period $t_2$-$t_3$ is a repeat cycle of the period $t_0$-$t_1$ and period $t_3$-$t_4$ is a repeat cycle of the period $t_1$-$t_2$. The simulation results corresponding to the system 100 for handling the peak power requirement of the medical imaging device 106 as depicted in FIGS. 8(*a*)-8(*c*) validate the method of FIG. 5. In particular, the simulation results of FIGS. 8(*a*)-8(*c*) demonstrate the handling of peak power requirement of the medical imaging device 106 via control of supply of any additional power demand from the energy storage device 110.

Furthermore, the foregoing examples, demonstrations, and process steps such as those that may be performed by the system may be implemented by suitable code on a processor-based system, such as a general-purpose or special-purpose computer. It should also be noted that different implementations of the present technique may perform some or all of the steps described herein in different orders or substantially concurrently, that is, in parallel. Furthermore, the functions may be implemented in a variety of programming languages, including but not limited to C++ or Java. Such code may be stored or adapted for storage on one or more tangible, machine readable media, such as on data repository chips, local or remote hard disks, optical disks (that is, CDs or DVDs), memory or other media, which may be accessed by a processor-based system to execute the stored code. Note that the tangible media may comprise paper or another suitable medium upon which the instructions are printed. For instance, the instructions may be electronically captured via optical scanning of the paper or other medium, then compiled, interpreted or otherwise processed in a suitable manner if necessary, and then stored in the data repository or memory.

Various embodiments of methods and systems for handling a peak power requirement of a medical imaging device are presented. In particular, the systems and methods presented herein allow efficient handling of peak power requirements of the medical imaging device by controlling supply of any additional power from the energy storage device used in conjunction with the medical imaging devices. Thus, the power source provides only average power of the peak power requirement of the medical imaging device. The use of the present systems and methods facilitates installation and use of higher power medical imaging devices with existing electrical installations at hospitals. Moreover, the present systems and methods permit retrofitting of the energy storage devices to existing MRI power architectures which employ LFPDUs. This retrofit aids in reducing the peak power demand from the AC mains and hence, effectively reduces the tariff on peak power. The methods and systems for handling the peak power requirement of the medical imaging device may find application in MRI devices, CT imaging devices, and the like.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof.

What is claimed is:

1. A method of handling a peak power requirement of a medical imaging device, the method comprising:
   measuring, using at least one controlling unit, a first voltage corresponding to a direct current link, a second voltage corresponding to one or more energy storage devices, or a combination thereof, wherein a power source is operatively coupled to a plurality of loads via the direct current link, and wherein the one or more energy storage devices are operatively coupled to the direct current link;
   comparing, using the at least one controlling unit, the first voltage with a first reference value and the second voltage with a second reference value, wherein the second reference value varies according to change of the measured first voltage; and
   regulating, using the at least one controlling unit, the first voltage and the second voltage based on the comparison to handle the peak power requirement of the medical imaging device.

2. The method of claim 1, wherein regulating the first voltage and the second voltage comprises transferring power between one or more of the power source, the direct current link, a power distribution unit, a first converter, the one or more energy storage devices, or combinations thereof.

3. The method of claim 2, wherein transferring the power comprises performing at least one of:
   conveying power from the power source to the direct current link via the power distribution unit;
   conveying power from the one or more energy storage device to the direct current link via the first converter; and conveying power from the direct current link to the one or more energy storage device via the first converter.

4. The method of claim 1, further comprising identifying occurrence of a first deviation of the first voltage from the first reference value, a second deviation of the second voltage from the second reference value, or a combination thereof, based on the comparison.

5. The method of claim 4, wherein regulating the first voltage comprises reducing the first deviation and regulating the second voltage comprises reducing the second deviation.

6. The method of claim 1, wherein the first voltage and the second voltage are a range of values having an upper limit and a lower limit.

7. The method of claim 1, wherein the first reference value is a fixed value, and the second reference value drops in response to drop of the first voltage at the peak power requirement.

8. The method of claim 1, wherein a relationship between the second reference value and the first voltage is a linear relationship.

9. The method of claim 1, wherein a relationship between the second reference value and the first voltage is an exponential relationship.

10. A system for handling a peak power requirement of a medical imaging device, the system comprising:
   a power source;
   a power distribution unit;
   a direct current link configured to operatively couple the power source to a plurality of loads;
   one or more energy storage devices operatively coupled to the direct current link;
   at least one controlling unit configured to:
      measure a first voltage corresponding to the direct current link, a second voltage corresponding to the one or more energy storage devices, or a combination thereof;
      compare the first voltage with a first reference value and the second voltage with a second reference value, wherein the second reference value varies according to change of the measured first voltage; and
      regulate at least one of the first voltage and the second voltage based on the comparison to handle the peak power requirement of the medical imaging device.

11. The system of claim 10, wherein the at least one controlling unit is further configured to identify occurrence of a first deviation of the first voltage from the first reference value, a second deviation of the second voltage from the second reference value, or a combination thereof, based on comparison.

12. The system of claim 10, wherein the power distribution unit is a high frequency power distribution unit, a low frequency power distribution unit, or a combination thereof.

13. The system of claim 10, wherein a first converter is operatively coupled between the one or more energy storage devices and the direct current link, and wherein the first converter comprises a bidirectional direct current to direct current converter.

14. The system of claim 10, wherein the power distribution unit comprises a second converter.

15. The system of claim 14, wherein the second converter is a rectifier, an active converter, an alternating current to direct current converter, or combinations thereof.

16. The system of claim 10, wherein the one or more energy storage devices comprise an ultra-capacitor bank, a capacitor bank, a battery, or combinations thereof.

17. The system of claim 10, wherein the plurality of loads comprises one or more of a gradient amplifier, a gradient control unit, a radio frequency transmit chain, a radio frequency receive chain of the medical imaging device.

18. The system of claim 10, further comprising a memory device which stores a predetermined relationship between the second reference value and the first voltage.

19. A controlling unit for handling a peak power requirement of a medical imaging device, comprising:
   a measurement subunit configured to measure a first voltage corresponding to a direct current link, a second voltage corresponding to one or more energy storage devices, or a combination thereof, wherein a power source is operatively coupled to a plurality of loads via the direct current link, and wherein the one or more energy storage devices are operatively coupled to the direct current link;
   a comparison subunit configured to compare the first voltage with a first reference value and the second voltage with a second reference value, wherein the second reference value varies according to change of the measured first voltage; and
   a regulating subunit configured to regulate the first voltage, the second voltage, or a combination thereof based on the comparison to handle the peak power requirement of the medical imaging device.

* * * * *